US008703209B2

(12) United States Patent
McCleary

(10) Patent No.: US 8,703,209 B2
(45) Date of Patent: Apr. 22, 2014

(54) COMPOSITION AND METHOD FOR MODULATING HYDROGEN ION PHYSIOLOGY

(76) Inventor: Edward Larry McCleary, Incline Village, NV (US)

(*) Notice: Subject to any disclaimer, the term of this patent is extended or adjusted under 35 U.S.C. 154(b) by 2300 days.

(21) Appl. No.: 11/088,388

(22) Filed: Mar. 23, 2005

(65) Prior Publication Data

US 2005/0181069 A1    Aug. 18, 2005

Related U.S. Application Data

(63) Continuation-in-part of application No. 10/462,958, filed on Jun. 17, 2003, now abandoned.

(51) Int. Cl.
*A01N 59/06* (2006.01)
*A01N 65/00* (2009.01)

(52) U.S. Cl.
USPC ............ 424/686; 424/725; 424/746; 424/756

(58) Field of Classification Search
None
See application file for complete search history.

(56) References Cited

U.S. PATENT DOCUMENTS

| | | | |
|---|---|---|---|
| 4,599,232 A | | 7/1986 | Bertelli |
| 5,397,786 A | * | 3/1995 | Simone ......................... 514/300 |
| 5,411,945 A | | 5/1995 | Ozaki et al. |
| 5,518,902 A | | 5/1996 | Ozaki et al. |
| 5,626,849 A | | 5/1997 | Hastings et al. |
| 5,744,161 A | | 4/1998 | Majeed et al. |
| 5,895,652 A | | 4/1999 | Giampapa |
| 5,948,430 A | | 9/1999 | Zerbe et al. |
| 5,973,004 A | | 10/1999 | Howard |
| 6,020,378 A | | 2/2000 | Cook et al. |
| 6,048,846 A | | 4/2000 | Cochran |
| 6,133,317 A | * | 10/2000 | Hart .............................. 514/574 |
| 6,156,355 A | | 12/2000 | Shields, Jr. et al. |
| 6,346,267 B1 | * | 2/2002 | Fry et al. ........................ 424/451 |
| 6,475,530 B1 | | 11/2002 | Kuhrts |
| 6,488,957 B1 | | 12/2002 | Koumarianos |
| 6,492,429 B1 | | 12/2002 | Graus et al. |
| 6,541,045 B1 | * | 4/2003 | Charters et al. ............... 424/737 |
| 6,572,897 B1 | | 6/2003 | Gorsek |
| 6,579,866 B2 | | 6/2003 | McCleary |
| 6,596,298 B2 | | 7/2003 | Leung et al. |
| 6,645,472 B1 | | 11/2003 | Anderson |
| 6,656,493 B2 | | 12/2003 | Dzija et al. |
| 7,445,807 B2 | * | 11/2008 | Lockwood ..................... 426/656 |
| 2002/0018832 A1 | | 2/2002 | Wong et al. |
| 2002/0146463 A1 | * | 10/2002 | Clayton ......................... 424/617 |
| 2002/0182196 A1 | | 12/2002 | McCleary |
| 2002/0183263 A1 | | 12/2002 | Hageman et al. |
| 2003/0031758 A1 | * | 2/2003 | Koss et al. ....................... 426/72 |
| 2003/0108645 A1 | | 6/2003 | Armand et al. |
| 2003/0139354 A1 | | 7/2003 | Buchholz et al. |
| 2003/0185918 A1 | | 10/2003 | Rosenbloom |
| 2004/0136922 A1 | | 7/2004 | Leung et al. |
| 2006/0039971 A1 | | 2/2006 | Lee et al. |

FOREIGN PATENT DOCUMENTS

| | | |
|---|---|---|
| DE | 4304394 | 9/1993 |
| EP | 1108363 A1 | 6/2001 |
| EP | 1108364 A2 | 6/2001 |
| EP | 1108365 A2 | 6/2001 |
| EP | 1161944 A | 12/2001 |
| EP | 1177729 A2 | 2/2002 |
| EP | 1269859 A2 | 1/2003 |
| RU | 2205655 C1 | 6/2003 |
| WO | WO-82/03986 A | 11/1982 |
| WO | WO-8901740 | 3/1989 |
| WO | WO-01/84961 A3 | 11/2001 |
| WO | WO-01/91734 A | 12/2001 |
| WO | WO-02/052955 A1 | 7/2002 |
| WO | WO-02/055069 A1 | 7/2002 |
| WO | WO-2006017551 A1 | 2/2006 |

OTHER PUBLICATIONS

M. Weger et al. Incomplete Renal Tubular Acidosis in primary osteoporosis, Osteoporosis. International (1999) 10:325-329.*
Schweiz et al. Latent Acidosis: Over acidification as a Cause of Chronic Diseases, Journal Suisse de medecine globale) 14:90-96(2002).*
James A. Duke, Ph.D., The Green Pharmacy: anti-aging Prescriptions, Rodale, 2001; p. 92-93.*
Krafte et al., Hydrogen Ion Modulation of Ca Channel Current in Cardiac Ventricular Cells, J. Gen. Physiol., The Rockefeller University Press, vol. 91 May 1988, 641-657.*
Sellmeyer et al., A high ratio of dietary animal to vegetable protein increases the rate of bone loss and the risk of fracture in postmenopausal women, Am. J Clin Nutr 2001; 73:118-22.*
Shin et al.; "A Prenylated Flavonol, Sophoflavescenol: A Potent and Selective Inhibitor of cGMP Phosphodiesterase 5"; Bioorganic & Medicinal Chemistry Letters; Sep. 2, 2002; pp. 2313-2316; 12(17) Elsevier Science Ltd.
Alpern et al.; "The clinical spectrum of chronic metabolic acidosis: homeostatic mechanisms produce significant morbidity"; American Journal of Kidney Diseases: the Official Journal of the National Kidney Foundation, vol. 29, No. 2, pp. 291-302; Feb. 1997.
Kenichi et al.; "Resveratrol Stimulates the Proliferation and Differentiation of Osteoblastic MC3T3-E1 Cells"; Biochemical and Biophysical Research Communications, Academic Press, Inc., Orlando, Florida; vol. 253, No. 3, pp. 859-863. Date: Dec. 30, 1998.
Szeto et al.; "Metabolic acidosis and malnutrition in dialysis patients"; Seminars in Dialysis; vol. 17, No. 5, pp. 371-375; Sep. 2004.

\* cited by examiner

*Primary Examiner* — Michael G Hartley
*Assistant Examiner* — Nabila Ebrahim
(74) *Attorney, Agent, or Firm* — Patton Boggs LLP

(57) ABSTRACT

Improved nutraceutical compositions and methods for maintaining healthy calcium metabolism and maintenance of muscle mass. The compositions include a first component selected from the group consisting of a citrate anion, a bicarbonate anion and an acetate anion; a second component selected from the group consisting of a potassium cation, a magnesium cation, a calcium cation, and a sodium cation; and a third component selected from the group consisting of resveratrol, green tea extract, tumeric, basil, sage, thyme, ginger or ginger extract, oregano or oregano extract, rosemary or rosemary extract, hypericum perforatum, glycyrrhiza glabra, plantago lanceolata, quercetin, glycyrrhiza glabra, and gingko biloba. The compositions may be administered conventionally in tablets or capsules, as a dietary supplement, or be delivered in a food additive, food or beverage product, functional food, medical food, botanical drug, over-the-counter (OTC) drug, or any other category of product for human or animal consumption.

7 Claims, No Drawings

COMPOSITION AND METHOD FOR MODULATING HYDROGEN ION PHYSIOLOGY

RELATED APPLICATIONS

This patent application is a continuation-in-part under 37 CFR 1.53(b) of U.S. patent application Ser. No. 10/462,958 filed Jun. 17, 2003, which application is incorporated by reference to the same extent as though fully disclosed herein.

BACKGROUND OF THE INVENTION

1. Field of the Invention

This invention relates in general to nutraceuticals, including functional foods, dietary supplements, nutritional supplements, medical foods, botanical drugs, and drugs. In particular, it relates to nutraceuticals and methods that are useful for supporting and promoting a healthy calcium and muscle physiology.

2. Statement of the Problem

Currently it is estimated that 10 million individuals have osteoporosis and another 34 million suffer from low bone density. If the effectiveness of prevention efforts does not improve, it is estimated that the public health cost of osteoporosis, including hospitalizations due to broken bones, will rise to $200 billion per year by 2040. The majority of current treatments are pharmaceutically based, such as Fosamax® and the statin category of drugs, or involves simple calcium or calcium/magnesium (Cal/Mag) supplementation. In spite of aggressive therapy, many patients do not respond or improve. Most therapies, even if effective, are limited by side effects. These therapies may be associated with enhanced urinary calcium loss and increased calcium-based urinary stone formation. Finally, even if a drug protocol is effective and without adverse effects for some sub-set of patients, this means that a synthetic drug must be taken every week for drugs such as Fosamax®, or every day for other drugs, for the rest of a patient's life—which could be three or four decades.

Muscle wasting also is on the rise in our society. It long has been associated with increasing age, though now it is recognized as a problem that begins much earlier. The therapy for this, up to now, has been limited to increasing food intake, focusing on protein, minerals and vitamins; that is essentially maintaining a healthy diet in older people.

To date, the etiology of dysfunctional calcium metabolism, muscle wasting, and similar related states is unknown. The optimal approach to such conditions is also unknown. A more physiologically based approach would provide the opportunity for a better chance of achieving and maintaining normal calcium and muscle homeostasis, and preventing and/or treating states of abnormal calcium and muscle physiology.

SUMMARY OF THE INVENTION

The invention solves the above and other problems by bringing together metabolic and medical knowledge not previously recognized as being related. A cohesive and holistic etiology that relates dysfunctional calcium metabolism and muscle wasting is introduced. It is recognized that both conditions are related to improper hydrogen ion balance (pH level) in the body. This recognition leads to insights that permit the formulation of compositions that are effective in treating both conditions.

The invention provides improved nutraceutical compositions and methods for maintaining healthy calcium metabolism, for preventing the development of states of abnormal calcium metabolism, for improving or treating such pathologic states of calcium metabolism, for maintaining bone health, for preventing calcium loss from bone, for treating conditions involving calcium loss from bone, such as osteoporosis and osteopenia, for improving bone healing and/or growth, for maintaining urinary health, for preventing calcium-containing stones, for treating calcium urolithiasis, for maintaining normal kidney function, for preventing deterioration of kidney function, for improving kidney function, and for treatment of lost kidney function; also for the prevention of loss of muscle and maintenance of muscle mass, for the enhancement of muscle mass, and for the treatment of conditions manifesting low muscle mass and/or loss of muscle mass; also for the maintenance of normal serum cortisol levels, for the prevention of increased serum cortisol levels, for the treatment of elevated cortisol levels, and for the lowering of serum cortisol levels; also involving conditions with adverse metabolic effects related to cortisol metabolism such as insulin resistance, obesity, high blood pressure, abnormalities in serum lipid concentrations, mental impairment, and the like.

The invention solves the problems discussed in the Background Of The Invention by providing novel compositions that address two different components of the metabolic pathway that leads to calcium dysfunction and muscle loss. First, it directly addresses the hydrogen ion level by providing anions and cations that reduce the acid level in the body. Secondly, it also addresses the prostaglandin component of the bone catabolic process by blocking this pathway component with cyclo-oxygenase (COX) inhibitors. This dual function of the compositions according to the invention is a key element of the invention.

The composition of the invention preferably also includes other ingredients which address other physiologic aspects of the bone and muscle health process. These include hormonal changes, homocysteine metabolism, inflammation, cortisol balance, micronutrient and macronutrient intake, and vitamin levels, intake, and activation.

The invention provides a composition for supporting and promoting healthy hydrogen ion balance, healthy calcium metabolism, and healthy muscle metabolism in the body of a human being, said composition comprising: a first component selected from the group consisting of a citrate anion, a bicarbonate anion and an acetate anion; a second component selected from the group consisting of a potassium cation, a magnesium cation, a calcium cation, and a sodium cation; and a third component selected from the group consisting of resveratrol, green tea extract, tumeric, basil, sage, thyme, ginger or ginger extract, oregano or oregano extract, rosemary or rosemary extract, hypericum perforatum, glycyrrhiza glabra, plantago lanceolata, quercetin, glycyrrhiza glabra, and gingko biloba; said first, second, and third components provided in an effective amount for supporting and promoting healthy hydrogen ion balance, healthy calcium metabolism, and healthy muscle metabolism in the body of said human being. Preferably, said second and third components are included in an ingredient selected from the group consisting of potassium citrate, potassium bicarbonate, potassium acetate, magnesium citrate, magnesium bicarbonate, magnesium acetate, calcium citrate, calcium bicarbonate, calcium acetate, sodium citrate, sodium bicarbonate, and sodium acetate. Preferably, said composition comprises $KHCO_3$ and Green Tea extract. Alternatively, the composition can comprise $KHCO_3$, $NaHCO_3$, and resveratrol. Another preferred composition comprises $KHCO_3$, $NaHCO_3$, resveratrol, and magnesium carbonate. A further preferred composition includes $KHCO_3$, $NaHCO_3$, basil, rosemary, oregano, and calcium. Still another preferred composition includes Kcitrate, KHCO$_3$, quercetin, and ginger. A further preferred composition comprises KHCO$_3$, NaHCO$_3$, rosemary, oregano, ginger, and resveratrol. The composition can further comprise an ingredient selected from the group consisting of folic acid, trimethylglycine, phosphatidyl choline, L-carnitine, acetyl L-carnitine, B vitamins, glyceryl phosphorylcholine, choline, SAMe (S adenosylmethionine), creatine, lipoic acid, coenzyme Q10, L-aspartic acid, serine, glycine and pyruvate. The composition can also include an ingredient selected from the group consisting of vitamin D (preferably vitamin D$_3$), vitamin K, vitamin C, vitamin B$_5$, boron, ipriflavone or other isoflavones, and branched chain amino acids (BCAA).

Any of the compositions according to the invention may be included in a delivery vehicle comprising a high protein food or beverage or a powder for making such a high protein food or beverage. Alternatively, the delivery vehicle may be selected from the group consisting of a soy protein and a whey protein; and a second vehicle selected from the group consisting of a vegetable, a fruit, and a berry. Another preferred delivery vehicle is one selected from the group consisting of an edible film, a breath-care strip, mint or lozenge, a food, a beverage, a spice, a condiment, and a salad dressing.

The invention also provides a method for supporting and promoting healthy hydrogen ion balance, healthy calcium metabolism, and healthy muscle metabolism in the body of a human being, said method comprising orally or parenterally administering to the human, for an effective period, a composition comprising: a first component selected from the group consisting of a citrate anion, a bicarbonate anion and an acetate anion; a second component selected from the group consisting of a potassium cation, a magnesium cation, a calcium cation, and a sodium cation; and a third ingredient selected from the group consisting of resveratrol, green tea extract, tumeric, basil, sage, thyme, ginger or ginger extract, oregano or oregano extract, rosemary or rosemary extract, hypericum perforatum, glycyrrhiza glabra, plantago lanceolata, quercetin, glycyrrhiza glabra, and gingko biloba; said method including administering said components in effective amounts for supporting and promoting healthy hydrogen ion balance, healthy calcium metabolism, and healthy muscle metabolism in the body of a human being. Preferably, said second and third components are provided by including in said composition an ingredient selected from the group consisting of potassium citrate, potassium bicarbonate, potassium acetate, magnesium citrate, magnesium bicarbonate, magnesium acetate, calcium citrate, calcium bicarbonate, calcium acetate, sodium citrate, sodium bicarbonate, and sodium acetate. Preferably, the method further comprises including in said composition an ingredient selected from the group consisting of folic acid, trimethylglycine, phosphatidyl choline, L-carnitine, acetyl L-carnitine, B vitamins, glyceryl phosphorylcholine, choline, SAMe (S adenosylmethionine), creatine, lipoic acid, coenzyme Q10, L-aspartic acid, serine, glycine and pyruvate. Preferably, said method further comprises including in said composition an ingredient selected from the group consisting of vitamin D (preferably vitamin D$_3$), vitamin K, vitamin C, vitamin B$_5$, boron, ipriflavone or other isoflavones, and branched chain amino acids (BCAA).

The invention not only provides a nutraceutical-based health composition and method of delivering it that effectively addresses calcium dysfunction and muscle wasting, but also does so without creating new problems. Numerous other advantages and features of the invention will become apparent from the following detailed description.

DETAILED DESCRIPTION OF THE PREFERRED EMBODIMENT

1. Overview

The prior art has stressed calcium supplementation as the cornerstone of a successful program for bone health. While calcium deficiency may be a risk factor for osteopenia, bone disorders are usually not cured by supplemental calcium. The invention recognizes this established knowledge, but takes the position that overly high calcium dosage does more harm than good.

Examination of evolutionary nutrition and its effects upon bone metabolism helps explain issues of bone health. Neanderthal nutritional modeling studies arrive at similar conclusions to those of direct studies of modern day hunter-gatherer cultures consuming their native diets. When interpreted from the perspective of dietary intake and its effect upon nutritional acid load to the body, great differences are noted between our "ancestral" diet and current dietary intake. Modern food choices expose us to a large acid load, day after day, throughout our lifetimes. In comparison, our evolutionarily based diet delivered a neutral, or even slightly alkaline, load. This contrasts starkly with modern cuisine. Recognition of this fact is one feature of the present invention.

The effect of chronic acid loading is to lower the pH of the blood. The pH in blood is metabolically regulated in a healthy individual and is kept within a narrow range. This is necessary because of the severe consequences of even minor pH changes. The appropriate bodily response to an acid load is to buffer the pH change. This buffering effect tends to restore pH to the normal range. This is a beneficial physiologic action and forms the basis for regulation of the pH in blood.

There is, however, a dark side to this process if it continues for an extended period of time. This is easily understood if the processes responsible for this buffering are investigated. The largest pool of acid buffer in the body is its carbonate reservoir. This resides almost exclusively in our bone mass where it is anchored by the mineral matrix. Calcium is one of these binding agents. As carbonate leaves the bone matrix, on its way to the blood stream where the pH buffering occurs, calcium is an unwilling participant in the same journey. This process, the simultaneous loss of bone calcium and carbonate, over time induces a slow, gradual progressive loss of bone mass and manifests itself as osteoporosis.

The calcium that leaves the bone reservoir also makes its way to the blood stream. Just as blood pH is carefully regulated, so is the blood calcium level. To prevent any significant rise in the blood calcium level, renal compensatory mechanisms are activated. These involve the loss of calcium in the urine. In this manner, the majority of the calcium lost from bone ends up in the urine. From this perspective it is easy to see why calcium supplementation is not the treatment of choice for osteoporosis. At best, it might only prevent calcium deficiency from developing. Indeed, many individuals on high dose calcium supplementation protocols develop calcium stones in their urinary tract.

Chronic nutritional metabolic acidosis may be viewed as an irritant to the body, much like infection or inflammation. According to the invention, the most logical treatment for osteoporosis is nutritional. Inappropriate dietary choices cause the calcium loss, so appropriate dietary choices may prevent the calcium loss. As explained above, this does not include high-dose calcium supplementation.

When, for any reason, appropriate dietary choices are impractical, then a backup plan that otherwise addresses the causative mechanism is indicated. This includes the use of dietary supplements that correct the diet-induced metabolic acidosis and its deleterious effects upon bone. Included in a preferred formulation is a potassium salt having an anion that is either bicarbonate or a metabolic precursor to a bicarbonate, such as a citrate. Potassium bicarbonate ($KHCO_3$) may be taken easily, is well tolerated, and immediately corrects the metabolic acidosis. This obviates the need for carbonate from bone to act as a buffer and physiologically remedies the problem of acidosis related bone loss.

A principle of the inventive analysis is that calcium dysfunction and muscle wasting are conditions that can only be addressed on a long-term basis. That is, if one waits until the conditions are manifest, it is generally too late to address the issues, at least over the short term. The invention also recognizes that the conditions are related, in that both have their roots in hydrogen ion imbalance. It also assumes that one cannot effectively address one without also considering the other. Finally, another important feature of the invention is that it is recognized that the traditional methods of addressing these issues, such as increasing the quantity of food containing calcium, protein, vitamins, and minerals in the diet, which essentially amounts to increasing the food intake, could lead to obesity if continued over the long term. Thus, the inventive etiology and resulting formulations are examined with a critical eye to make certain that, in correcting calcium dysfunction and muscle wasting, we do not introduce another problem. In the discussion below, the various factors that the inventor has determined relate to hydrogen imbalance are brought together to suggest formulations that address the above issues in a holistic fashion.

As mentioned above, a key aspect of the analysis is the consideration that chronic metabolic acidosis (CMA) has a well-established potential for a catabolic effect upon bone. It results in hypercalciuria and negative calcium balance attributable to calcium efflux from bone. It is associated with metabolic bone disease and calcium nephrolithiasis. In animal models, CMA results in a decrease in bone calcium, increase in bone resorption, and reduced trabecular bone volume. In vitro studies have demonstrated that metabolic acidosis is both a potent stimulator of bone resorption and an inhibitor of bone formation. This suggests that CMA acts directly at the tissue level to affect bone metabolism. Indirect mechanisms may also exist.

As suggested above, a premise of the invention is that modern Western-type diet in humans is a cause of lifelong mild CMA. This contributes to bone catabolism due to the delivery of an obligatory daily acid load. Although still within the broad range of normal values, plasma bicarbonate concentration decreases progressively under such conditions of increased endogenous acid production. The homeostatic regulation of a stable pH, i.e., a stable hydrogen ion concentration, is of critical importance for mammalian survival. A gain of acid initiates a physiologic response that ultimately leads to the net excretion of acid to correct the imbalance. As suggested above, as the first line of defense, bone appears to be instrumental in helping to buffer changes in blood pH. However, this homeostatic function of the skeleton occurs at the expense of bone mineral content, and thus bone density, and results in enhanced urinary calcium loss.

It is hypothesized that physico-chemical, hormonal, and cell-mediated processes contribute to the acid-induced bone loss. Bone calcium efflux appears to be related to the local concentration of bicarbonate anion; that is, the lower the bicarbonate, the greater the calcium efflux. The invention contemplates that an intervention capable of augmenting bicarbonate will slow down, reduce, or diminish skeletal calcium loss.

Acidosis also has multiple effects upon cells, one of which is to increase levels of prostaglandins. Prostaglandin $E_2$ ($PGE_2$) has been implicated in this setting. $PGE_2$ has been shown to stimulate bone resorption in organ culture and to mediate calcium efflux in response to a variety of cytokines and growth factors. The invention contemplates that components of the cell-mediated effector mechanism of bone loss are responsible for $PGE_2$ secretion, and that an acidic environment facilitates this response. That is, acid-induced, cell-mediated calcium efflux from bone is regulated, at least partly, by an increase in endogenous $PGE_2$ production. This sequence of steps further suggests that acidosis and $PGE_2$ secretion act sequentially in the same pathway. This forms the basis for a new approach to healthy bone metabolism. By enhancing bicarbonate levels as discussed above, the acid portion of the process is addressed. If, in addition, by inhibiting synthesis and secretion of $PGE_2$, calcium efflux is further inhibited, a dual approach may be formulated that improves bone health. A corollary of this facilitated approach is the reduction of calcium loss in the urine with a concordant decrease in calcium stone formation. A similar approach may be utilized to enhance bone healing and/or bone growth.

The invention contemplates that the prostaglandin step is blocked by cyclo-oxygenase (COX) inhibitors. These may be pharmaceuticals or they may be naturally occurring substances or combinations thereof. Nutraceuticals that are useful as cyclo-oxygenase (COX) inhibitors include resveratrol, green tea extract, tumeric, basil, sage, thyme, ginger or ginger extract, oregano or oregano extract, rosemary or rosemary extract, hypericum perforatum, glycyrrhiza glabra, plantago lanceolata, quercetin, glycyrrhiza glabra, and gingko biloba.

Dietary salt, i.e., sodium chloride, is known to enhance urinary calcium excretion. Yet it is poorly appreciated that the anion accompanying sodium is important to the overall effect of salt on calcium metabolism. Acetate, citrate, or bicarbonate, as opposed to chloride, improves urinary calcium loss and blood pH. Provision of potassium and magnesium cations is also associated with improved acid-base balance and calcium balance.

The concept presented here is that CMA, which is usually, but not always, related to dietary etiology, when allowed to persist for years or decades, even if mild, leads to subtle but progressive and serious bone demineralization over a lifetime. If addressed early on in its course, it should be amenable to physiologic therapeutic intervention. By correcting the underlying reasons for the abnormality in calcium metabolism, an improved response with fewer adverse effects is expected. It is also suggested that even in states of abnormal calcium metabolism not associated with CMA, these same interventions or approaches would be beneficial.

The long-term consequence of a small change in calcium balance is substantial. A 50 mg increase in urinary calcium loss per day, which is not uncommon, results in an 18 gram loss in a year, or 360 grams over 20 years. Since the average adult female skeleton contains 750 grams of calcium at its peak, this represents the loss of about half of total skeletal calcium stores. The effects of CMA may be greater as we age because aging kidneys cannot generate ammonium ions and excrete hydrogen ions as well as younger kidneys do. This puts even greater stress on the buffering capacity of bone.

Such an approach to CMA forms the basis for the current inventive concept. That is, the invention provides agents that prevent and/or reverse CMA over the long term. These agents may be augmented by other synergistic agents including pharmaceutical, nutraceutical, or botanical ingredients to form the inventive compositions. These compositions may be administered orally, intravenously, or parenterally. These compositions may be supplied as tablets, capsules, powders, chewables, or any other common delivery system. They may be delivered in a food additive, food or beverage product, functional food, dietary supplement, medical food, botanical drug, over-the-counter (OTC) drug, or any other category of product for human beings regulated by the Food and Drug Administration (FDA) which may be created or defined in the future. They may take any product form: powdered shake, health drink, protein bar, meal replacement, edible film, food coating, or lozenge.

Because the mechanism of intervention simultaneously lowers urinary calcium losses, urolithiasis will be diminished and or prevented. In addition, because calcium wasting will be minimized, there will be an improvement in bone healing and bone growth. This would improve healing after orthopedic surgeries, especially in osteopenic individuals, and would accelerate bone healing after traumatic injuries. It would also be expected to improve bone quality in metabolic bone diseases such as Osteogenesis Imperfecta (OI) and other similar conditions.

Importantly, the invention notices that in disorders that cause CMA, protein degradation in skeletal muscle is accelerated. The production of nitrogen (N) end products that are excreted in the urine is increased. Such effects produce negative N balance which is associated with muscle wasting. This disturbance of N metabolism appears to be a direct result of the CMA. The muscle loss occurs because of induction of processes that contribute to muscle degradation without commensurately increasing the rate of protein synthesis. This proteolytic effect has been attributed to two acidosis-related disturbances in skeletal muscle cells: stimulation of an ATP- and ubiquitin-dependent proteolytic pathway and enhancement of the oxidation of proteolytically released branched chain amino acids (valine, leucine, and isoleucine), thus preventing their uptake for protein synthesis.

Additional mechanisms operate during CMA to facilitate renal excretion of ammonium and promote N wasting. The hepatic synthesis of glutamine is increased and it is transported to the kidney where it fuels the increased production of ammonium excreted in the urine as the carrier of the hydrogen ions. Hence, this acid-induced proteolysis is an acid-base homeostatic mechanism. By releasing increased amounts of glutamine which are used in the synthesis of ammonium ions, the kidney is then able to excrete more hydrogen ions and mitigate the severity of the acidosis.

The above adaptations, if persistent, are detrimental. They include decreased renal citrate production and excretion, hypercalciuria, dissolution of bone, protein catabolism and muscle wasting, and progression of renal disease.

The dual approach of both addressing the acid imbalance and blocking the prostaglandin step is the most important aspect of the invention. However, the invention goes further and also addresses other physiologic processes that are indirectly related to calcium dysfunction and muscle loss. Examples of other physiologic mechanisms which can also conspire to impair calcium, bone, and insulin metabolism include hormonal changes, homocysteine metabolism, inflammation, cortisol balance, micronutrient and macronutrient intake, and vitamin levels, intake, or activation.

The invention also recognizes that glucocorticoids play an important role in the physiological response to systemic acidosis. In adrenalectomized animals, glucocorticoids increase net acid excretion. In humans, metabolic acidosis results in a corticotrophin-dependent increase in corticosteroids. In turn, the increase in glucocorticoids with acidosis is necessary for many of the physiological responses to acidosis: increased ammonium excretion, increased titratable acid, and increased proximal renal tubule sodium-hydrogen ion (Na+/H+) exchange (NHE). Supporting these contentions, it is not surprising that adrenalectomized animals fail to respond appropriately to metabolic acid loads in terms of ammonium and phosphate excretion. This failure may be corrected with the administration of the synthetic glucocorticoid dexamethasone. It is postulated that the interaction between acidosis and glucocorticoids is necessary for the normal functioning of the NHEer. It is also apparent that an interaction between acidosis and glucocorticoids exists not only in kidney, but in muscle and bone as well.

Two isoenzymes of 11 β-hydroxysteroid dehydrogenase (11 β-HSD1 and 11 β-HSD2) catalyze the interconversion of hormonally active cortisol and inactive cortisone. The past decade has seen an exponential increase in research focusing on 11 β-HSD1 principally because of its role in human obesity and insulin resistance, and in other disorders in which glucocorticoids have been implicated, such as osteoporosis. Increased activity of 11 β-HSD1 up-regulates the tissue level of the hormone cortisol. Hence, inhibitors of this enzyme would act in an analogous fashion to other interventions that directly lower cortisol levels.

Consistent with this is the observation that overexpression of 11 β-HSD1 in adipose tissue is associated with acquired obesity and features of insulin resistance. Polymorphisms of 11 β-HSD1 in Pima Indians are associated with Type 2 diabetes independently of obesity. Hence, interventions able to beneficially modulate tissue cortisol exposure, or serum cortisol concentrations, would be expected to promote leanness and enhance insulin sensitivity. Excessive hydrogen ion concentration produces a stress to the body which is associated with an increase in serum cortisol levels. A fall in serum cortisol is associated with neutralization of this acidotic state. Hence, compositions that may safely buffer excessive hydrogen ions act to simultaneously normalize glucocorticoids. This should decrease body fat accumulation and insulin resistance. The current disclosure, therefore, includes ingredients that act to lower elevated cortisol levels, maintain healthy cortisol levels, and prevent the elevation of cortisol levels. This improves intraperitoneal and subcutaneous fat content.

Elevated levels of the hormone cortisol, often caused by stress or lack of exercise, or both, or administration of synthetic analogs such as prednisone, decadron, methylprednisolone, and the like, have also been associated with accelerated bone demineralization, thwarted growth, poor bone healing, and osteopenia. In particular, CMA has been associated with elevations of morning cortisol levels and increases in free-cortisol measured in a 24-hour urine collection. Both of these findings are associated with enhanced bone loss. These findings exemplify indirect mechanisms whereby CMA enhances bone loss.

A further feature of the invention is that it recognizes that skeletal bone loss is associated with inflammatory processes, although it takes a different approach to this aspect of the problem than the prior art. It is believed that the statin category of drugs ameliorates osteoporosis by an anti-inflammatory mechanism. Pro-inflammatory transcription factors AP-1 and NFKB play a role. By limiting reductive stress and its subsequent effects upon AP-1 and NFKB, MUT (Metabolic Uncoupling Theory—see prior patent application Ser. No. 10/462,958 cited above) acts in a similar anti-inflammatory fashion. The invention leaps from this fact to the recognition that a complete program addressing bone health should include a formulation to treat the inflammatory component of the disorder. Such a composition includes a combination of such agents used in association with additional agents that specifically address the metabolic acidosis. The chosen anti-inflammatory agents should be well tolerated orally, complement calcium metabolism, have a good safety profile, and be active in bone and muscle tissue metabolism. Such agents include: folic acid, trimethylglycine, phosphatidyl choline, L-carnitine, acetyl L-carnitine, B vitamins, glyceryl phosphorylcholine, choline, SAMe (S adenosylmethionine), creatine, lipoic acid, coenzyme Q10, L-aspartic acid, serine, glycine and pyruvate.

Additional agents which augment bone and/or muscle metabolism by various unrelated or not well-understood mechanisms include vitamin D (preferably vitamin $D_3$), vitamin K, vitamin C, vitamin $B_5$, boron, ipriflavone or other isoflavones, and branched chain amino acids (BCM). These agents may be added in various combinations to the prior formulations to augment and/or supplement the beneficial actions previously discussed.

In addition, when the bone and muscle metabolism agents according to the invention are used in certain applications or for individuals with specific concerns in addition to the bone and muscle concerns mentioned above, additional ingredients may be added to address those applications and concerns. For example, for meal replacement applications, soymilk may be used as a vehicle to administer the compositions of the invention. As another example, if a person is highly active, glucose may be added for energy, and if the person desires to add significant muscle and bone mass, taurine and glutamine may be added. If a person is trying to lose weight while enhancing bone and muscle metabolism, Vitex agnus-castus, biotin, garcinia cambogia, chrominum polynicotinate, and medium chain triglycerides (MCT) may be added. For ingredients that are useful for the above and other applications and concerns, see U.S. patent application Ser. No. 10/462,958 referred to above.

2. Formulations

There are two categories of agents that, when combined as directed, form the basis for the compositions and methods of administration. Category 1 includes agents that, based on the above analysis, are specifically designed to directly ameliorate CMA without causing new problems. Category 2 agents are chosen because of their ability to inhibit the COX enzyme, and thus indirectly ameliorate CMA. These are preferably combined with other agents, or combinations thereof, that are designed to further improve hydrogen ion metabolism or mitigate the effects of CMA. They are generally given as daily doses, or servings, either one or several times per day. They are usually given for a prolonged period of time, usually, but not always, for months or years.

A person skilled in the art will use clinical experience, results of the individuals DEXA Scan or other bone mass density test, results of the individual's blood and urine analysis, medical literature and training, as well as the desired outcome to develop a specific formulation. Any formulation will include at least one agent from category 1A below, at least one agent from category 1B below, and at least one agent from category 2.

Category 1A

|  | Amount | Preferred Amount |
| --- | --- | --- |
| Citrate anion | 10 mg to 25 g | 1 g to 10 g |
| Bicarbonate anion | 10 mg to 25 g | 1 g to 10 g |
| Acetate anion | 10 mg to 25 g | 1 g to 10 g |

Category 1B

|  | Amount | Preferred Amount |
| --- | --- | --- |
| Potassium cation | 10 mg to 10 g | 200 mg to 5 g |
| Magnesium cation | 10 mg to 4 g | 400 mg to 2 g |
| Calcium cation | 10 mg to 6 g | 500 mg to 2 g |
| Sodium cation | 10 mg to 10 g | 200 mg to 2000 mg |

It should be understood that the anions and cations summarized above are normally provided together in a single complex, such as potassium citrate, potassium bicarbonate, potassium acetate, magnesium citrate, magnesium bicarbonate, magnesium acetate, calcium citrate, calcium bicarbonate, calcium acetate, sodium citrate, sodium bicarbonate, sodium acetate, and related compounds. However, they may also be provided separately.

Category 2

|  | Amount | Preferred Amount |
| --- | --- | --- |
| Resveratrol | 100 mcg to 2 g | 500 mcg to 500 mg |
| Green tea extract | 1 mg to 2 g | 10 mg to 1000 mg |
| Turmeric | 1 mg to 2 g | 25 mg to 1000 mg |
| Basil | 1 mg to 5 g | 40 mg to 2000 mg |
| Sage | 1 mg to 5 g | 20 mg to 2000 mg |
| Thyme | 1 mg to 5 g | 10 mg to 2000 mg |
| Ginger/Ginger extract | 1 mg to 4 g | 20 mg to 2000 mg |
| Oregano/Oregano extract | 1 mg to 4 g | 30 mg to 2000 mg |
| Rosemary/Rosemary extract | 1 mg to 4 g | 40 mg to 2500 mg |
| Hypericum perforatum | 100 mcg to 1000 mg | 5 mg to 500 mg |
| Glycyrrhiza glabra | 100 mcg to 2 g | 5 mg to 500 mg |
| Plantago lanceolata | 100 mcg to 3 g | 5 mg to 500 mg |
| Quercetin | 1 mg to 5 g | 10 mg to 2000 mg |
| Gingko biloba | 1 mg to 2 g | 10 mg to 1000 mg |

EXAMPLE 1

This represents a formulation to enhance bone formation in a young Caucasian female with a positive family history for osteoporosis. The list represents one serving delivered in a compressed tablet. Two servings per day each day should be consumed.

| $KHCO_3$ | 500 mg |
| --- | --- |
| Green Tea extract | 200 mg |

EXAMPLE 2

This represents a formulation for a post-menopausal female with normal bone density designed to promote healthy skeletal function. The list represents one serving to be given in two capsules. Two capsules are to be taken orally twice a day each day. The individual should have DEXA scans every three to four years to determine the length of time she should continue to take the formulation.

| | |
|---|---|
| KHCO₃ | 600 mg |
| NaHCO₃ | 1200 mg |
| Resveratrol | 2 mg |

EXAMPLE 3

This represents a formulation for a post-menopausal female with a positive family history for skeletal calcium loss and low bone density. The list represents one serving to be given in two capsules. She should take two capsules three times a day throughout her remaining lifetime.

| | |
|---|---|
| KHCO₃ | 500 mg |
| NaHCO₃ | 1200 mg |
| Basil | 25 mg |
| Rosemary | 30 mg |
| Oregano | 25 mg |
| Vitamin D₃ | 200 IU |
| Calcium (chelated) | 400 mg |
| Vitamin K | 50 mcg |
| Boron | 500 mcg |
| Vitamin C | 25 mg |
| Vitamin B₅ | 5 mg |

If bone density continues to fall, the following should be added (per serving):

| | |
|---|---|
| Resveratrol | 1 mg |
| Green tea extract | 30 mg |
| Magnesium (chelated) | 250 mg |
| Trimethylglycine | 250 mg |
| L-Carnitine | 10 mg |
| Phosphatidyl Choline | 200 mg |
| Ginger | 50 mg |
| Turmeric | 100 mg |
| Folic acid | 400 mcg |

EXAMPLE 4

This is a formulation for a 45-year-old male taking calcium citrate and having recurrent calcium urinary tract stone formation. The list represents one serving and is taken in a capsule. He should take one capsule twice a day for as long as he takes the calcium citrate.

| | |
|---|---|
| KHCO₃ | 500 mg |
| NaHCO₃ | 300 mg |
| Ginger | 50 mg |
| Vitamin D₃ | 100 IU |

If after two months he still is forming stones, he should take two capsules twice a day.

EXAMPLE 5

This is a formulation for a hypogonadal 63-year-old male with low bone density who has had difficulty healing a right wrist fracture. The list represents one serving and is taken in two capsules. He is to take two capsules twice per day as long as it takes to heal the fracture adequately.

| | |
|---|---|
| Kcitrate | 200 mg |
| KHCO₃ | 200 mg |
| Quercetin | 50 mg |
| Vitamin D₃ | 75 IU |
| Vitamin K | 50 mcg |
| Calcium (chelated) | 400 mg |
| Magnesium (chelated) | 200 mg |
| Ginger | 400 mg |

EXAMPLE 6

This is a formulation for a 55-year-old female with small bone structure and a history of multiple fractures. The list is for one serving of a meal replacement. It is to be taken once or twice per day.

| | |
|---|---|
| Soy milk | 8 ounces |
| Ipriflavone | 100 mg |
| KHCO₃ | 500 mg |
| NaHCO₃ | 1000 mg |
| Calcium (chelated) | 1000 mg |
| Magnesium (chelated) | 400 mg |
| Vitamin D₃ | 500 IU |
| Vitamin K | 2 mg |
| Vitamin C | 50 mg |
| Boron | 1 mg |
| Rosemary | 25 mg |
| Oregano | 10 mg |
| Ginger | 25 mg |
| Resveratrol | 2 mg |
| Vitamin B₅ | 15 mg |
| Folic acid | 400 mcg |
| Trimethylglycine | 750 mg |
| Phosphatidyl Choline | 500 mg |
| L-Carnitine | 10 mg |
| Natural vanilla flavor | 20 mg |

EXAMPLE 7

This is an example of a composition to be consumed by a post-menopausal female who cannot tolerate hormonal therapy and with declining bone density. The list of amounts and ingredients constitutes one serving. One or several servings may be consumed daily.

| | |
|---|---|
| KHCO₃ | 500 mg |
| NaHCO₃ | 750 mg |
| Magnesium carbonate | 400 mg |
| Vitamin D₃ | 100 IU |
| Vitamin K | 100 mcg |
| Vitamin C | 50 mg |
| Ginger | 20 mg |
| Turmeric | 15 mg |
| Basil | 25 mg |
| Vitamin B₅ | 15 mg |
| Folic acid | 200 mcg |
| Resveratrol | 100 mcg |
| Trimethylglycine | 100 mg |

Calcium may be added to this composition as follows:

| | |
|---|---|
| Calcium citrate | 800 mg |

Oregano and/or Rosemary may also be added as follows:

| | |
|---|---|
| Oregano | 25 mg |
| Rosemary | 10 mg |

EXAMPLE 8

The following composition is suitable for a young weight training individual, especially someone on a high protein diet which delivers high levels of acid to the body. By neutralizing the acid, there will be lowered cortisol levels and less muscle catabolism. The ingredients and amounts constitute one serving. One or several servings may be taken each day.

| | |
|---|---|
| $KHCO_3$ | 600 mg |
| $NaHCO_3$ | 1800 mg |
| Magnesium carbonate | 300 mg |
| Resveratrol | 500 mcg |

For a more efficacious composition, the following may be included:

| | |
|---|---|
| Vitamin $B_5$ | 20 mg |
| Vitamin C | 50 mg |
| Green tea extract | 100 mg |
| Folic acid | 200 mcg |
| Trimethylglycine | 500 mg |
| L-Carnitine | 100 mg |
| Sage | 20 mg |
| Thyme | 10 mg |
| Rosemary | 20 mg |
| Oregano | 30 mg |

Additional ingredients may include:

| | |
|---|---|
| Creatine | 4 g |
| Lipoic acid | 100 mg |
| Glucose | 10 g |
| Coenzyme Q10 | 50 mg |
| Branched Chain Amino Acid mixture | 3 g |
| Taurine | 200 mg |
| Glutamine | 200 mg |

This composition will work well embedded into a soy, or other type, protein shake. It may also be delivered in fruit or vegetable based beverages. Similar formulations for bone health may be delivered in a similar fashion.

EXAMPLE 9

A composition that enhances weight loss and at the same time addresses hydrogen ion issues includes the following ingredients and amounts per serving. One or more servings may be consumed per day.

| | |
|---|---|
| $KHCO_3$ | 350 mg |
| $NaHCO_3$ | 900 mg |
| Magnesium carbonate | 250 mg |
| Calcium citrate | 500 mg |
| Green tea extract | 100 mg |
| It may also include: | |
| *Vitex agnus-castus* | 50 mg |
| Or: | |
| Biotin | 300 mcg |
| L-carnitine | 10 mg |
| *Garcinia cambogia* | 100 mg |
| L-aspartic acid | 2 g |
| Chromium polynicotinate | 400 mc |
| Or: | |
| Medium chain triglycerides | 4 g |
| Or: | |
| Trimethylglycine | 400 mg |
| Folic acid | 150 mcg |
| Vitamin $B_5$ | 10 mg |
| Vitamin C | 25 mg |

This formulation can be particularly effective when delivered via a shake, bar, or meal replacement type drink.

EXAMPLE 10

The formulations taught by this disclosure, such as the formulations taught in Example 7, may be included in other delivery systems. Although protein from both animal and plant sources adds acid to the diet, and acid has an adverse impact upon both bone and muscle metabolism, it has a beneficial impact as well. When higher amounts of protein are fed to animals or humans, Insulin-Like Growth Factor 1 (IGF-1) levels increase. IGF-1 has a hormonal anabolic effect upon bone and muscle tissue. Therefore, if protein is given in conjunction with the formulations listed herein, then IGF-1 levels (which are bone and muscle growth factors) rise. This is good for both bone and muscle growth. The acid load delivered by the additional protein consumption is "neutralized" by the various formulations disclosed herein. Thus, this combination simultaneously increases bone and muscle formation while blocking muscle and bone breakdown. This double approach is an important feature of this disclosure.

Hence, the formulations disclosed herein may be included in soy, whey, or other protein containing delivery systems such as shakes, bars, powders, drinks, and the like.

There are also foods, such as spices, fruits, and vegetables that have alkalinizing effects. The various formulations discussed in this patent, as well as related compositions not explicitly described, may be effectively combined with such foods, and combinations thereof. These foods may also be mixed with protein containing delivery systems. Examples of this include: a soy protein and vegetable mixture; and a whey protein and fruit and/or berry mixture.

The delivery vehicle may also comprise an edible film, a breath-care strip, mint or lozenge, or a food, water, beverage, spice, condiment, salad dressing, or other functional food. The preferred foods are: energy bars, salad dressings, condiments (such as steak sauce, mustard, catsup, and soy sauce), vegetable oils, fruit products such as jellies, jams, and syrups, cereals, trail mix, cookies, pasta, flours including wheat, soy, oat, and potato flour, whey, chocolate, yogurt, tofu, bagels, baked goods, vegetables, soups, trail mix, nutritional bars, snacks, crackers, meats, meat products such as lunch meats, and milk products such as ice cream, cheese, and butter. The term "beverage" is used in its common meaning, which does not include water or medicines. The preferred beverages are sports drinks, soft drinks, alcoholic beverages, tea, coffee, milk, and fruit juices. For details of such delivery vehicles, see U.S. patent application Ser. No. 10/890,067 filed Jul. 12, 2004 and entitled Foods, Beverages, Condiments, Spices And Salad Dressings With Specialized Supplements, and U.S. patent application Ser. No. 11/049,244 filed Feb. 2, 2005 and entitled Delivery System And Method For Supporting And Promoting Healthy Sexual Function And Prevention And Treatment Of Sexual Dysfunction, which patent applications are hereby incorporated by reference as though fully disclosed herein.

Embodiments in accordance with the invention have been described herein mainly with reference to human physiology and metabolism. The invention is generally useful and widely applicable in mammalian physiology and veterinary medicine. Examples of useful applications include enhancement of bone and muscle mass in greyhounds or racehorses, and slower deterioration of bone structure maintenance in household pets.

It should be understood that the specific formulations and methods described herein are exemplary and should not be construed to limit the invention, which will be described in the claims below. Further, it is evident that those skilled in the art may now make numerous uses and modifications of the specific embodiments described, without departing from the inventive concepts. Also, the invention contemplates that formulations in accordance with the invention may be made with combinations of the disclosed ingredients other than those described above as long as they are within the scope of the claims below. There are many other variations of clinical and metabolic situations, specific methods of addressing such situations, and formulations and compositions than can be included in a document such as this. Consequently, the invention is to be construed as embracing each and every novel feature and novel combination of features present in and/or possessed by the compositions and methods described and claimed and by their equivalents.

The invention claimed is:

1. A method for supporting and promoting bone healing in a human being in need thereof, said method comprising orally or parenterally administering to the human, for an effective period, a composition comprising the following components: $KHCO_3$, $NaHCO_3$, $MgCO_3$, folic acid, vitamin D, vitamin $B_5$, turmeric, basil, sage, thyme and rosemary; and said method including administering said components in effective amounts for supporting and promoting bone healing in a human being in need thereof.

2. A method as in claim 1 wherein said composition further comprises an ingredient selected from the group consisting of potassium acetate, magnesium bicarbonate, magnesium acetate, and sodium acetate.

3. A method as in claim 1, said method further comprising including in said composition an ingredient selected from the group consisting of trimethylglycine, phosphatidyl choline, L-carnitine, acetyl L-carnitine, glyceryl phosphorylcholine, choline, SAMe (S adenosylmethionine), creatine, lipoic acid, coenzyme Q10, L-aspartic acid, serine, glycine and pyruvate.

4. A method as in claim 1, said method further comprising including in said composition an ingredient selected from the group consisting of vitamin K, vitamin C, boron, ipriflavone or other isoflavones, and branched chain amino acids (BCAA).

5. A method as in claim 1, said method further comprising including said composition in a delivery vehicle comprising a high protein food or beverage or a powder for making such a high protein food or beverage.

6. A method as in claim 1, said method further comprising including said composition in a delivery vehicle comprising: a first vehicle selected from the group consisting of a soy protein and a whey protein; and a second vehicle selected from the group consisting of a vegetable, a fruit, and a berry.

7. A method as in claim 1, said method further comprising including said composition in a delivery vehicle comprising a vehicle selected from the group consisting of an edible film; a breath-care strip, mint, or lozenge; a food, a beverage, a spice, a condiment, and a salad dressing.

* * * * *